United States Patent [19]

Larkin et al.

[11] Patent Number: 4,980,503

[45] Date of Patent: Dec. 25, 1990

[54] CONVERSION OF GLYCOL FORMATES TO MONOCARBOXYLIC ACIDS

[75] Inventors: John M. Larkin; George P. Speranza, both of Austin, Tex.

[73] Assignee: Texaco Inc., White Plains, N.Y.

[21] Appl. No.: 896,683

[22] Filed: Aug. 15, 1986

Related U.S. Application Data

[63] Continuation-in-part of Ser. No. 685,933, Dec. 24, 1984, abandoned.

[51] Int. Cl.$^5$ .................... C07C 51/12; C07C 53/124; C07C 53/126
[52] U.S. Cl. .................... 562/517; 260/413; 549/377; 560/232
[58] Field of Search ................ 562/517, 606; 260/413

[56] References Cited

FOREIGN PATENT DOCUMENTS 1072979  1/1960  Fed. Rep. of Germany ...... 562/606

*Primary Examiner*—Vivian Garner
*Attorney, Agent, or Firm*—Jack H. Park; Kenneth R. Priem; Carl G. Ries

[57] ABSTRACT

It has been surprisingly discovered in accordance with the present invention that glycol formates and their alkyl ether derivatives can be substantially selectively converted to monocarboxylic acids by bringing a glycol formate or an alkyl ether derivative thereof into contact with a bed of activated carbon in the presence of carbon monoxide and a halide promoted group VIII soluble transition metal catalyst optionally in the presence of a solvent.

20 Claims, No Drawings

CONVERSION OF GLYCOL FORMATES TO MONOCARBOXYLIC ACIDS

RELATED APPLICATIONS

This application is a continuation-in-part of copending Larkin application Ser. No. 06/685,933 filed Dec. 24, 1984, now abandoned and entitled "Conversion of Glycol Formates to Carboxylic Acids".

BACKGROUND OF THE INVENTION

1. Field of the Invention

This invention relates to a method for the production of monocarboxylic acids. More particularly, this invention relates to the conversion of glycol formates to monocarboxylic acids including propionic acid, isobutyric acid and/or n-butyric acid. In particular, the present invention is directed to a process wherein a glycol formate or an alkyl derivative thereof is brought into contact with activated carbon in the presence of carbon monoxide, a soluble compound of a group VIII transition metal catalyst and a halide promoter whereby the glycol formate is preferentially converted to a corresponding monocarboxylic acid having one additional carbon atom in the molecule derived from the carbon monoxide. There is a preferential conversion to monocarboxylic acids because there is no apparent formation of detectable quantities of polycarboxylic acids.

2. Prior Art

Wakamatsu et al. in U.S. Pat. No. 3,798,267 discloses the preparation of acetic acid by contacting methyl formate with activated carbon in the presence of a halide promoter and carbon monoxide.

Antoniades U.S. Pat. No. 4,194,056 also discloses a process for the preparation of acetic acid from methyl formate. In accordance with the Antoniades process, the methyl formate is brought into contact with a soluble rhodium salt catalyst in the presence of carbon monoxide and a halogen promoter.

Isogai U.S. Pat. No. 3,839,426 is more broadly directed to the preparation of organic carboxylic acids from formic acid esters, such as vinyl formate (Example 36) by contacting the formic acid ester with a group VIII or group IIb catalyst in the presence of carbon monoxide.

French Patent No. 2,030,118 discloses a process wherein carboxylic acids, especially formic acid, are produced from methanol by reacting methanol and carbon monoxide over a solid activated carbon bed at a temperature of from 200° to about 500° C. and a pressure of about 100 to about 3000 psi (7–210 Kg/cm$^2$) using a halogen promoter which is either dispersed on the carbon bed or incorporated as a component of the catalyst system.

Copending coassigned U.S. patent application Ser. No. 478,830 filed Mar. 25, 1983, now abandoned in the name of John M. Larkin and entitled "A Process for Alkanol Carbonylation to Carboxylic Acids Using the Novel Combination of Catalyst and Carbon Bed Components" discloses a process wherein an alkanol together with a halide promoter and a low concentration of a soluble metal catalyst is passed over a carbon bed in the presence of carbon monoxide.

Copending coassigned U.S. patent application Ser. No. 478,829 filed Mar. 25, 1983, now abandoned in the name of John M. Larkin and Roger G. Duranleau and entitled "A Process for Producing Carboxylic Acids by Carbonylation of Alkanols Over a Carbon Catalyst" discloses a process wherein an alkanol and a halide promoter are passed over a carbon bed contained in a nickel or cobalt alloy reactor in the presence of carbon monoxide.

SUMMARY OF THE INVENTION

It has been surprisingly discovered in accordance with the present invention that when a glycol formate or an alkyl derivative thereof is brought into contact with a bed of activated carbon in the presence of carbon monoxide and a halide promoted group VIII soluble transition metal catalyst, optionally in the presence of a solvent, the reaction product comprises carboxylic acids; the carboxylic acid component consisting essentially of monocarboxylic acids which are selectively formed in preference to polycarboxylic acids. That is to say, the carboxylic acids that are formed are monocarboxylic acids corresponding to the glycol formate and detectable quantities of polycarboxylic acids, such as dicarboxylic acids, are not detected.

DETAILED DESCRIPTION OF THE INVENTION

The starting materials for the present invention are glycol formates or their alkyl ether derivatives, carbon monoxide, activated carbon, a soluble compound of a group VIII transition metal, and a halide promoter.

The glycol formate starting material to be used in accordance with the present invention may be represented by the following formula:

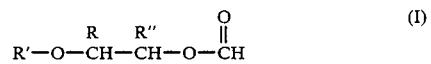

Where R and R" represent H or $-CH_3$;
R' represents H, or R''', or

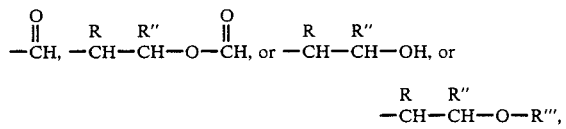

and
R''' represents a $C_1$ to $C_{12}$ alkyl group.

Examples of suitable glycol formates include ethylene glycol monoformate, ethylene glycol diformate, propylene glycol monoformate, propylene glycol diformate, diethylene glycol monoformate, diethylene glycol diformate, dipropylene glycol monoformate, dipropylene glycol diformate, ethylene glycol monomethyl ether formate (2-methoxyethanol formate), ethylene glycol monoethyl ether formate (2-ethoxyethanol formate), the formates of ethylene glycol monopropyl ether, ethylene glycol monobutyl ether, ethylene glycol monohexyl ether, ethylene glycol monododecyl ether, propylene glycol monomethyl ether, propylene glycol monoethyl ether, propylene glycol monopropyl ether, propylene glycol monobutyl ether, etc.

The catalysts that are suitable for use in the practice of the present invention are compounds of group VIII transition metals that are soluble in the formate to be used. The soluble metal catalyst may be chosen from a wide variety of organic and inorganic compounds, complexes, etc. as will be shown and illustrated below. It is only necessary that the catalyst precursor actually employed contain a group VIII transition metal in a soluble state.

Effective metals include cobalt, ruthenium, iron, nickel, rhodium, palladium, osmium, iridium and platinum. The soluble group VIII transition metal catalyst may be added to the reaction mixture in the form of a carbonyl as in the case of, for example, triruthenium dodecacarbonyl, dicobalt octacarbonyl, iron pentacarbonyl, nickel tetracarbonyl, diiron nonacarbonyl, tetracobalt dodecacarbonyl, etc. Alternately, the group VIII metal may be added as the salt of a mineral acid as in the case of, for example, ruthenium trichloride, iron (II) iodide, iron (III) nitrate, cobalt (II) nitrate, cobalt (II) chloride, nickel (II) iodide, etc. or as the salt of a suitable organic carboxylic acid such as, for example, cobalt (II) acetate, cobalt (III) acetate, nickel (II) propionate, iron (II) naphthenate, etc. As additional examples, the metal may be added to the reaction mixture as a complex with a trisubstituted phosphorous compound or as a salt of an enolate. Representative examples include cobalt (III) 2,4-pentanedionate and dichlorotris (triphenylphosphine)ruthenium(II), etc.

Preferred group VIII soluble transition metal catalysts include carbonyls and halides. Among the particularly preferred are cobalt and nickel compounds such as dicobalt octacarbonyl, cobalt diiodide, nickel dichloride, etc.

Another effective method of adding small quantities of group VIII transition metals is to dissolve the group VIII transition metal in the reaction medium as for example by contacting the reactants and halide promoters with nickel or cobalt alloys. A particularly preferred method of introducing the soluble group VIII metal by this procedure is to use a reactor, pumps, or conduits constructed of nickel or cobalt alloys where the nickel or cobalt constitute from about 2% to about 98% of the metal content of the alloy. Commercial nickel stainless steel or Hastelloy alloys are especially preferred. Among these suitable alloys may be mentioned 316 Stainless Steel and Hastelloy C alloys.

The catalyst need not be present except as a minor constituent of the total reaction mixture. Thus, effective results are obtainable when the group VIII metal constitutes from about 10 to about 1000 parts per million of the total reaction mixture, such as about 50 to about 150 ppm.

The halide promoter, which may suitably be an alkyl halide, should be present in a larger concentration, such as a concentration of about 1 to about 20 mol percent, based on the glycol formate. The halide promoting component of the catalyst system may be introduced into the reaction zone in liquid form or gaseous form or dissolved in a suitable solvent or reactant. Satisfactory halide promoters include hydrogen halides such as hydrogen iodide and gaseous hydriodic acid, alkyl halides containing 1 to 12 carbon atoms such as methyl iodide, ethyl iodide, 1-iodopropane, 2-iodobutane, 1-iodobutane, methyl bromide, ethyl bromide, benzyl iodide; dihalomethanes such as diiodomethane and acyl halides such as acetyl iodide may also be used. Other examples include the quaternary ammonium and phosphonium halides, examples of which include tetramethyl ammonium iodide, tetra butyl phosphonium iodide, etc. Alkali and alkaline earth halides, such as cesium iodide, may also be used.

The carbon monoxide will normally be fed to the reaction zone in the form of a gas and may be used alone or in conjunction with up to 90% by volume of one or more other gases. These other gases may include inert gases such as nitrogen, argon, neon, etc. Hydrogen may also be present, but a part of the carbon monoxide will tend to react with the hydrogen thus rendering that part ineffective for the purpose of the present invention.

The activated carbon bed over which the liquid feed stream is passed can be a fixed or fluidized bed and is prepared from a porous solid. The density range of the solid should be about 0.03–2.5 $cm^3/gm$. A preferred density range is 0.05–1.5 $cm^3/g$. A fixed carbon bed can be prepared from porous carbon by pyrolysis of amorphous carbon. Activated carbons of this type have surface areas of 200–2000 $m^2/g$. Carbons can be preformed of compacted granules, powders, or particles. Animal, vegetable or petroleum sources can be used.

The activated carbon bed can optionally be washed to remove metallic components which may be present from the organic sources used to prepare the carbon. If washed, the treatment consists of a HF solution or $HNO_3$ solution where the ratio is about 600 to about 1000 ml of $HNO_3$ per 500 g carbon and the $HNO_3$ concentration in water is from about 2%–30%. If HF is used, the concentration in water should be from about 10–55%. Washing time may be from 5 minutes to 24 hours. Further, the acid washed carbon can be washed with $H_2O$ to remove excess acid.

Suitable sources of activated carbon which can be used in the process of this invention include NORIT® RB-1 or SORBONORIT® B-3 activated carbon.

NORIT® and SORBONORIT® are registered trademarks of the American Norit Company. Another suitable activated carbon which may be used is CARBORUNDUM® GAC-616G. CARBORUNDUM® is a registered trademark of Kennecott Corporation. These activated carbons, prepared by the manufacturers according to procedures developed by them, are in the form of granules or pellets, and are described as generally having a surface area of 1000–1200 $m^2/g$. Methods of manufacturing activated carbon are listed in the book: *Activated Carbon, Manufacture and Regeneration* by A. Yehaskel, Noyes Data Corporation, Park Ridge, N.J., 1978.

The quantity of soluble transition metal catalyst employed in the instant invention is not critical and may vary over a wide range. Metal concentrations can range from less than 5 (e.g., 1) to greater than 1000 ppm, depending on the activity of the metal species. In general, the process of the present invention is desirably conducted in the presence of a catalytically effective quantity of the active metal species, in conjunction with a halide promoter, and optionally in the presence of a solvent which gives the desired products in reasonable yields. The reaction proceeds when employing as little as about 0.0001 wt. %, and even lesser amounts of group VIII transition metal catalyst together with about 1–50 wt. % of a halide promoter, basis the total weight of the reaction mixture. The upper concentration is dictated by a variety of factors including catalyst cost, partial pressures of carbon monoxide, operating temperature, etc. A soluble group VIII transition metal catalyst concentration of from about 0.002 to about 0.02 wt. % metal in conjunction with an alkyl halide promoter concentration of from about 5 to about 15 mol percent based on the total mols of reaction mixture is generally desirable in the practice of this invention.

Although a solvent is not necessary for the reactions to occur, a solvent may be provided for instance to cause better solubility of promoters or to facilitate product separation. Suitable solvents include carboxylic acids such as acetic, propionic, butyric, and isobutyric acids, hydrocarbons such as cyclohexane, toluene, n-decane and the like, and ketones such as acetone, 2-butanone, or 4-methyl-2-pentanone. Other suitable solvents may include the organic chlorides such as chlorobenzene, chlorocyclohexane, 1-chlorohexane, etc. Preferred solvents are carboxylic acids such as propionic and butyric acids. When employing a solvent, it may be provided in concentrations of 5-80% and preferably in concentrations of 10-60% based on the weight of the glycol formate.

A fluidized carbon bed or ebullient carbon bed is prepared by providing agitated contact of the activated carbon particles with the mixture of reactant liquids and gases as for example by suspending the carbon particles in the gas/liquid stream.

The reaction is also suitably conducted using a reactor, such as a jacketed reactor, containing a bed of activated carbon over which the other reactants are passed.

After passing through the reactor, the reactants may be separated into unreacted feed components and products by any suitable means such as vacuum distillation.

The temperature to be used in conducting the reaction of the present invention is a variable which is dependent upon other reaction parameters including pressure, the concentration and choice of the particular species of soluble group VIII transition metal catalysts, etc. In general, temperatures within the range of about 170° to about 400° C., e.g. about 200° C. to about 400° C. or about 200° C. to about 360° C. are employed with superatmospheric pressures of carbon monoxide. A narrower temperature range of 240-350° C. is preferred.

Superatmospheric pressures of 100 psi or greater lead to substantial yields of carboxylic acids by the process of this invention. A preferred operating range is from 500 psi to 4000 psi, e.g. about 1500 to about 2100 psig, although pressures above 4000 psi also provide useful yields of desired carboxylic acids.

In all these syntheses utilizing glycol formates of Formula I where R' equals H or

the amount of carbon monoxide present in the reaction mixture should be from about 5% to about 50% on a mole basis of the amount of glycol formate present. Preferably about 0.1 to about 0.3 moles of carbon monoxide per mole of glycol formate are used. When an alkyl ether derivative of a glycol formate is used (R' equals R''' in Formula I) the moles of carbon monoxide present should, however, be in excess of the number of moles of alkyl ether derivative present. Suitable amounts of carbon monoxide are 1.05-2.00 moles per mole of alkyl ether glycol formate. Preferably, about 1.2 to about 1.8 moles of carbon monoxide per mole of glycol ether formate are used.

Residence time is another variable which may be used in controlling the course of the reaction. When the reaction is conducted batch-wise in an autoclave, reaction times may suitably be within the range of about 1 to about 24 hours. When the reaction is conducted continuously, by passing the reactants over a bed of activated carbon, the liquid hourly feed rate may suitably be within the range of about 0.02 to about 1.0 pounds of reactants per hour per pound of catalyst (w/hr/w).

The reaction product will comprise unreacted gaseous and liquid feed components and a variety of gaseous and liquid reaction products, such as water, methyl formate, formic acid, ethanol, acetic acid, methyl acetate, ethylene, ethane, isobutyraldehyde, dioxane, propionic, butyric and pentanoic acids and esters thereof, etc. The monocarboxylic acids have an additional carbon atom derived from the carbon monoxide. There is no formation of detectable quantities of polycarboxylic acid, such as dicarboxylic acids.

SPECIFIC EXAMPLES

1. Reaction of Propylene Glycol Diformate, Diiodomethane, and Co(III) 2,4-Pentanedionate with CO Continuously Over Activated Carbon. (5711-22)

A solution of 900 g of propylene 91glycol diformate*, 100 g of $CH_2I_2$, and 0.40 g Co(III) 2,4-pentanedionate was pumped continuously at 0.16 ml/min for 66 hours and at 0.26 ml/min for six hours through a stainless steel conduit with a pump having stainless steel wetted parts to a reactor constructed of Hastelloy C and containing 25 cc of Sorbonorit ® B-3 activated carbon. Carbon monoxide was also fed to the reactor at 2 liters/hour. The reactor was maintained at elevated temperatures and pressures. Results of glc effluent analyses are shown in Table I.

*The propylene glycol diformate was made by treating propylene glycol with excess formic acid and azeotropic removal of $H_2O$ in the presence of $CHCl_3$. Analysis indicates 6.0% HCOOH, 0.4% $CHCl_3$, 0.6 unknowns, 5.5% of propylene glycol monoformate, 86.6% of propylene glycol diformate, and 0.9% of a heavy unknown.

It should be noted that there is excellent conversion and that particularly at 250° C., a very high ratio of isobutyric/n-butyric acid and esters is obtained.

2. Reaction of Propylene Glycol Diformate with CO in the Presence of Benzyl Bromide and Cobalt (III) 2,4-Pentanedionate Over Sorbonorit B-3 Activated Carbon. (5711-34)

A similar procedure was employed as for Example 1 except 75.03 g of benzyl bromide replaced the $CH_2I_2$ and only 740 g of propylene glycol diformate were used. The reactor liq. rate was 0.16 ml/min, pressure was 2250 psig, and average temperature was about 260° C. Analysis of components in the liquid effluent showed that the major g.c. peak occurs at the retention time of n-butyric acid; only small amounts (less than 2%) isobutyric acid could be present. There were also major peaks for water, formic acid and benzyl bromide. The spectrum did not include detectable peaks for dicarboxylic acids, although the detection of such peaks was sought.

Analysis of gas effluent showed that of the heavy gaseous components, isobutyraldehyde and n-butyraldehyde were 12 and 4 A % respectively.

TABLE I

Organic Analysis, %

TABLE I-continued

| Ex. | °C. | Pres. psig | Liquid Feed Rate ml/min | HCOOH | iPrOH | HOAc[1] | iPrO—CH(=O) |
|---|---|---|---|---|---|---|---|
| 1 | 250 | 2175 | 0.16 | 21.8 | 24.1 | 15.0 | 10.6 |
| 2 | 238 | 2200 | 0.16 | 1.6 | 3.1 | 14.6 | 2.7 |
| 3 | 230 | 2200 | 0.16 | 7.1 | 4.7 | 8.9 | 9.0 |
| 4 | 230 | 1700 | 0.16 | 9.4 | 10.5 | 8.4 | 9.1 |
| 5 | 225 | 1950 | 0.26 | No valid sample analyses | | | |

[1]Derived from $CH_2I_2$

| Ex. | i-Butyric Acid | n-Butyric Acid | iPr i-Butyrate | iPr n-Butyrate | iPr I |
|---|---|---|---|---|---|
| | | Organic Analysis A% | | | |
| 1 | 20.5 | ND[1] | 2.5 | 1.1 | 2.2 |
| 2 | 30.8 | 28.0 | 5.2 | 5.1 | 2.1 |
| 3 | 26.8 | 18.0 | 7.4 | 6.0 | 4.2 |
| 4 | 21.2 | 15.1 | 8.7 | 6.8 | 4.0 |
| 5 | No valid sample analyses | | | | |

[1]Not detected by the analytical method

3. Reaction of Diethylene Glycol (DEG) Diformate/Diethylene Glycol Monoformate Continuously over Activated Carbon in the Presence of CO, $CH_2I_2$, and Soluble Nickel Catalyst. 5633–51; 5633–49

A mixture consisting of 62% DEG diformate, 22% DEG monoformate, 4% $H_2O$, and 7% HCOOH was prepared by mixing excess HCOOH with DEG, and then repeatedly adding chloroform and distilling to remove a $CHCl_3/H_2O$ azeotrope.

A solution of 1500 g of this mixture and 95 g of diiodomethane was pumped continuously at 0.15 ml/min through a stainless steel conduit and by use of a pump with stainless steel wetted parts to a 25 cc Hastelloy C reactor containing 25 cc of Sorbonorit ® B-3 activated carbon. [From earlier work use of this reactor system, its pump and associated metal conduits, is known to provide low levels (<115 ppm) of soluble nickel species in solution.] Carbon monoxide at 2 liters/hr was simultaneously fed to the reactor, which was maintained at elevated temperatures and pressure. Analyses of liquid effluents at the various conditions were as follows:

TABLE II

| | | Percent by Gas-Liquid Chromatography[1] | | | | | |
|---|---|---|---|---|---|---|---|
| Temp. °C. | Pres. psig | $H_2O$ | EtOH | HCOOH | HOAc[2] | C—C—COOH | (dioxane ring) |
| 265 | 1800 | 19.0 | 2.6 | 6.1 | 7.7 | 35.5 | 18.0 |
| 245 | 1800 | 71.2 | 1.7 | 2.1 | 3.1 | 20.0 | 0.8 |
| 245 | 1400 | 66.4 | 1.9 | 1.8 | 3.7 | 23.5 | 0.7 |

[1]Dicarboxylic acids were not detected.
[2]The HOAc is derived from $CH_2I_2$.

Analysis of effluent collected at 265° and 1800 psig was also performed by gas chromatography-Fourier Transform infra-red. The following components were identified (A % given) $H_2O$ (20), $CH_3CHO$ (2), EtOH (6), HCOOH (2), HOAc (7), EtOAc (3), C-C-COOH (34),

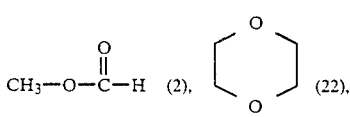

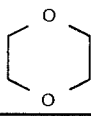

unknown unsaturated aldehyde (1), unknown ketone (1).

Off-gas analysis was performed from gaseous effluent when the reactor was maintained at 1800 psig and 245° C. Analysis as follows (glc mole %), $H_2$ (5.9), $CO_2$ (43.3), $C_2H_4$ (21.1), $C_2H_6$ (0.5), air contaminant (1.3), $CH_4$ (0.2), CO (22.1), $H_2O$ (3.9), $C_3H_8$ (0.2), $C_3H_6$ (0.5), isobutyraldehyde (0.2).

4. Continuous Reaction of DEG Diformate in the Presence of CO, $CH_2Br_2$, and Cobalt(III) 2,4-pentanedionate over Activated Carbon. (5633–96)

A mixture consisting of 93.8% DEG diformate, 3.1% DEG monoformate, 0.98% $CHCl_3$, and 1.5% was prepared from DEG, excess HCOOH and using $CHCl_3$ for azeotropic removal of $H_2O$. A solution consisting of 820.8 g of this DEG diformate, 173.9 g $CH_2Br_2$, and Co(III) 2,4-pentanedionate (0.25 g) was used as the liquid feed in the same reactor-conduit-pump system as was used for Example 3. The reactor contained 25 cc of Sorbonorit B-3 activated carbon. Carbon monoxide at 2 liters/hour was simultaneously metered to the reactor; pressure was maintained at 1600–1800 psig. Liquid feed rate was 0.16 ml/min. Reactor temperature was varied from 235° C. to 265° C. Liquid effluent was periodically sampled and analyzed. Analyses at several different temperatures were as follows: (glc A %)

TABLE III[1]

| Temperature | DEG Derivatives[2] | C—C—COOH | (dioxane ring) |
|---|---|---|---|
| 235° C. | 66.7 | 1.1 | None Detected |
| 250° C. | 25.6 | 18.2 | 26.6 |

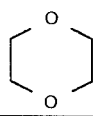

TABLE III[1]-continued

| Temperature | DEG Derivatives[2] | C—C—COOH | 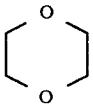 |
|---|---|---|---|
| 265° C. | 5.1 | 13.9 | 55.3 |

[1]No detectable dicarboxylic acid.
[2]Primarily a mixture of mono- and diformates of diethylene glycol. Dicarboxylic acids were not detected.

Typical off-gas analysis (at 237° C. and 1800 psig) was as follows: 0.9% $H_2$, 7.5% $CO_2$, 0.5% $C_2H_4$, 0.02% $C_2H_6$, 0.6% air contaminant, 0.1% $CH_4$, 83.7% CO.

This example indicates that conversion is markedly dependent on temperature, but that the dioxane/propionic acid ratio increases as a result of temperature.

It also indicates the suitability of a bromide promoter in the presence of activated carbon.

5. Reaction of DEG Diformate Continuously over Activated Carbon in the Presence of CO, Acetyl Bromide, and Co(III) Acetylacetonate. (5711–42)

The procedure of Example 4 was essentially repeated except the liquid feed consisted of 450 g DEG diformate, 40.0 g acetyl bromide, 0.225 g Co acetylacetonate, and the feed rate was 0.15 ml/min. Reactor pressure and temperature were varied systematically. Analyses of liquid samples were as follows:

TABLE IV

| Temp °C. | Pres. psig | % C—C—COOH | % Dioxane | % DEG[1] Derivatives |
|---|---|---|---|---|
| 245 | 1400 | 4.5 | 9.5 | 72.1 |
| 250 | 2250 | 15.6 | 27.4 | 39.3 |
| 276 | 1400 | 3.6 | 13.5 | 66.7 |

[1]Primarily mono- and diformates of diethylene glycol. Dicarboxylic acids were not detected. Water constituted the principal inorganic product.

Typical off-gas analysis (sampled at 252° C. and 2250 psig) as follows: 9.5% $H_2$, 26.3% $CO_2$, 10.2% $C_2H_4$, 0.2% $C_2H_6$, 5.8% air contaminant, 0.3% $CH_4$, 53.5% CO, 4.6% heavies.

6 Reaction of 2-methoxyethanol Formate with CO over Activated Carbon in the Presence of Hydrogen Iodide and Trace Quantities of Nickel. (5633–30; 5633–44)

The reaction of 3.28 moles of 2-methoxyethanol with 17.5 moles of formic acid in the presence of 2 ml. of $BF_3 \cdot Et_2O$ at room temperature for six days yielded a liquid of the following composition (glc A %): $H_2O$=12.1, HCOOH=38.4, 2-methoxyethanol=4.3, 2-methoxyethanol formate 42.3%. This solution was mixed with 57% aqueous HI in a weight ratio of 1187 g/175 ml respectively. It was pumped continuously at 0.17 ml/min through a stainless steel conduit and by use of a pump with stainless steel wetted parts to a 25 cc Hastelloy C reactor containing 25 cc of Sorbonorit® B-3 activated carbon. From earlier work use of this reactor system, its pump and associated metal conduits, is known to provide low levels (<115 ppm) of soluble nickel species in solution. Carbon monoxide at 2 liters/hr was simultaneously fed to the reactor which was maintained at elevated temperatures and pressures. Analyses of liquid effluents at various conditions were as follows:

TABLE V

| | | glc A % | | | |
|---|---|---|---|---|---|
| Temp. °C. | Pres. psig | $H_2O$ | Acetic Acid | Propionic Acid | 2-methoxy ethanol formate |
| 1. 282 | 2250 | 53.7 | 22.7 | 21.3 | None |
| 2. 283 | 1700 | 54.2 | 23.0 | 21.6 | None |
| 3. 264 | 1700 | 54.3 | 21.7 | 22.2 | None |

Proton nmr was performed on a sample of product collected under the first set of conditions. It showed only $H_2O$ and approximately equimolar quantities of acetic and propionic acids. Off-gas analysis performed on gaseous effluent under the second set of conditions was as follows: 30.5 mole % $CO_2$, 0.6% $C_2H_4$, 1.2% $C_2H_6$, 11.7% air (contaminant), 8.4% $CH_4$, 38.2% CO, 1.3% $H_2O$, 0.1% $C_3H_6$.

This example illustrates the high selectivity and productivity possible under several sets of conditions and the non-necessity for using a purified alkoxyethanol formate feed solution.

7. Reaction of 2-n-butoxyethanol Formate with CO over Activated Carbon in the Presence of Methyl Iodide, and Dicobalt Octacarbonyl. (5633–52; 5633–58)

2-n-Butoxyethanol formate was prepared in 96% purity by reaction of 2-n-butoxyethanol with excess formic acid and azeotropic removal of $H_2O$ in the presence of chloroform. To 480 g there was added 100 g of a solution consisting of 300 ml $CH_3I$, 20 ml acetic acid, and 0.05 g of $Co_2(CO)_8$. The resultant solution was pumped at 0.17 ml/min to a 25 cc reactor containing 25 cc of Sorbonorit B-3 (same system as Example 6) while CO was simultaneously fed to the reactor at 5 or 7.5 liters/hr. The reactor was operated at elevated temperature and pressure. GLC analyses of liquid effluent collected under various conditions were as follows:

TABLE VI

| | | | glc A %[5] | | | | |
|---|---|---|---|---|---|---|---|
| Temp °C. | Pres. psig | CO, l/hr | $H_2O$ | HOAc[2] | EtCOOH | BuEF[1] | Pentanoic[3] Acids |
| 1. 275 | 2000 | 5 | 4 | 11 | 6 | 7 | 12 |
| 2. 243 | 2025 | 5 | 5 | 5 | N.D.[4] | 17 | 6 |
| 3. 295 | 2600 | 7.5 | 6 | 16 | 42 | 0.5 | 17 |
| 4. 295 | 2000 | 5 | 7 | 11 | 53 | 0.6 | 14 |

[1]2-n-butoxyethanol formate
[2]In feedstock and from methyl iodide
[3]2-methylbutyric acid and n-pentanoic acid
[4]Not determined by analytical method because of interfering substance
[5]No detectable dicarboxylic acids Effluent samples from Conditions 3 and 4 were analyzed more extensively by gas chromatography/Fourier transform infrared technique. They are labeled 5633-58-11 and 5633-58-13, respectively, and represent a complete analysis of the reaction products. Their analyses are reproduced below as Tables VII and VIII. Note the absence of detectable dicarboxylic acid.

Typical off-gas produced (e.g., from condition 4) analyzed as follows (glc mole %): $H_2=1.5$, $CO_2=15.8$, $C_2H_4=3.1$, $C_2H_6=1.4$, air contaminant $=0.6$, $CH_4=0.3$, $Co=63.96$, heavies$=13.3$. Heavies analysis as follows (glc A %) unknown$=6.8$, $C_3H_6=4.1$, $H_2O=18.4$, $CH_3OH=1.7$, butene$=9.3$, butane$=56.8$ (remainder unidentified).

This example illustrates the temperature dependence of the desired reaction to form propionic and pentanoic acids.

TABLE VII

Sample 5633-58-11

| GC/IR Spectrum Number | A % | Identification or Classification |
|---|---|---|
| 1 | | Reference |
| 2 | 0.1 | Carbon dioxide |
| 3, 4 | 8.1 | Water |
| 5 | | Reference |
| 6, 7 | 0.3 | Ethanol |
| 8 | | Reference |
| 9, 10 | 0.3 | Ethyl formate |
| 11 | | Reference |
| 12, 13 | 1.3 | Carbon dioxide - breakdown of formic acid |
| 14, 15 | 1.8 | Ethyl acetate |
| 16, 17 | 14.9 | Acetic acid |

TABLE VII-continued

Sample 5633-58-11

| GC/IR Spectrum Number | A % | Identification or Classification |
|---|---|---|
| 18 | | Reference |
| 19 | 0.2 | Predominately acetic acid carryover |
| 20, 21, 22 | 4.4 | Ethyl propionate |
| 23, 24, 25 | 40.5 | Propionic acid |
| | | Reference |
| 26 | 1.2 | Butyl acetate |
| 27, 28, 29, 30 | 8.3 | Propionic acid esters - not any of the common esters such as methyl, ethyl, propyl or butyl |
| 31, 32, 33 | 9.6 | 2-Methyl butyric acid + unknown ester |
| 34, 35 | 5.9 | Pentanoic acid |
| 36, 37 | 0.99 | |
| 38, 39 | 0.4 | Unidentified esters of propionic, butyric or pentanoic acid |
| 40 | 0.2 | Reference |
| 41 | | |
| 42 | 0.1 | |
| 43, 44 | 0.4 | |

TABLE VIII

Sample 5633-58-13

| GC/IR Spectrum Number | A % | Identification or Classification |
|---|---|---|
| 1 | | Reference |
| 2 | 0.03 | Air |
| 3, 4, 5 | 1.7 | Carbon dioxide + water |
| 6 | 0.2 | Spectrum not usable |
| 7 | | Reference |
| 8 | 0.2 | Ethanol |
| 9 | | Reference |
| 10 | 0.1 | Acetone |
| 11 | 0.3 | Methyl acetate |
| 12 | | Reference |
| 13 | | Reference |
| 14 | front bottom of peak | Ethyl acetate |
| 15, 16, 17, 18 | 15.4 | Acetic acid |
| 19 | 0.1 | Acetic acid carryover + unknown |
| 20 | 2.9 | Ethyl propionate |
| 21, 22, 23 | 48.4 | Propionic acid |
| 24 | | Reference |
| 25 | 0.1 | Unidentified acetate + propionic acid |
| 26, 27, 28 | 7.4 | Propionic acid esters - not any of the common esters such as methyl, ethyl, propyl or butyl |
| 29, 30, 31 | 12.8 | 2-Methylbutyric acid |
| 32, 33, 34 | 7.6 | Pentanoic acid |
| 35 | | Reference |
| 36 | 0.1 | |
| 37 | | |

TABLE VIII-continued

Sample 5633-58-13

| GC/IR Spectrum Number | A % | Identification or Classification |
|---|---|---|
| 38 | 0.9 | |
| 39 | 0.4 | Unidentified esters of propionic, butyric or pentanoic acid Reference |
| 40 | | |
| 41 | | |
| 42 | 0.2 | |

The foregoing examples have been given by way of illustration only and are not intended as limitations on the scope of this invention, which is defined by the following appended claims.

What is claimed is:

1. A process for preparing monocarboxylic acids which comprises the steps of bringing a glycol formate or an alkyl ether derivative thereof into contact with activated carbon in the presence of carbon monoxide and a catalyst system consisting essentially of a soluble group VIII transition metal catalyst and a hydrogen halide, an alkyl halide or a benzyl bromide promoter to thereby provide a reaction product containing monocarboxylic acids but not a detectable quantity of polycarboxylic acids, said monocarboxylic acids being derived from the glycol of said glycol formate or said alkyl ether derivative thereof and containing an additional carbon atom derived from reaction of the formate group of said glycol formate or said alkyl ether derivative thereof and said carbon monoxide, said glycol formate and said alkyl ether derivative having the formula:

$$R'-O-\underset{R}{C}H-\underset{R''}{C}H-O-\overset{O}{\underset{\|}{C}}H \quad (I)$$

where R and R" represent H or —CH$_3$;
R' represents H, or R''', or $$\overset{O}{\underset{\|}{C}}H, \quad -\overset{O}{\underset{\|}{C}}H-\underset{R''}{C}H-O-\overset{O}{\underset{\|}{C}}H, \text{ or } -\underset{R}{C}H-\underset{R''}{C}H-OH, \text{ or}$$

$$-\underset{R}{C}H-\underset{R''}{C}H-O-R''',$$

R''' represents a C$_1$ to C$_{12}$ alkyl group.

2. A process as in claim 1, wherein the glycol formate is brought into contact with the activated carbon at a temperature within the range of about 200° to about 360° C. and a pressure within the range of about 1500 to about 2100 psig.

3. A process as in claim 2 wherein, in formula (I), R' represents H or $$-\underset{\|}{\overset{O}{C}}H,$$

the group VIII transition metal catalyst is a cobalt catalyst and the halide promoter is an iodide or a bromide.

4. A process as in claim 3, wherein the glycol formate is propylene glycol diformate, the halide promoter is CH$_2$I$_2$ and the catalyst is cobalt (III) 2,4-pentanedionate.

5. A process as in claim 3, wherein the glycol formate is propylene glycol diformate, the halide promoter is benzyl bromide and the catalyst is cobalt (III) 2,4-pentanedionate.

6. A process as in claim 2 wherein, in the formula, R and R" represent H, R' represents:

$$-\underset{R}{C}H-\underset{R''}{C}H-O-\overset{O}{\underset{\|}{C}}H, \text{ or } -\underset{R}{C}H-\underset{R''}{C}H-OH$$

the group VIII transition metal catalyst is a nickel catalyst, and the halide promoter is CH$_2$I$_2$.

7. A process as in claim 2 wherein, in the formula, R and R" represent H, R' represents:

$$-\underset{R}{C}H-\underset{R''}{C}H-O-\overset{O}{\underset{\|}{C}}H, \text{ or } -\underset{R}{C}H-\underset{R''}{C}H-OH$$

the group VIII transition metal catalyst is cobalt (III) 2,4-pentanedionate and the halide promoter is CH$_2$Br$_2$.

8. A process as in claim 2 wherein, in the formula, R and R" represent H, R' represents:

$$-\underset{R}{C}H-\underset{R''}{C}H-O-\overset{O}{\underset{\|}{C}}H, \text{ or } -\underset{R}{C}H-\underset{R''}{C}H-OH$$

the group VIII transition metal catalyst is cobalt (III) 2,4-pentanedionate and the halide promoter is benzyl bromide.

9. A process as in claim 2 wherein, in the formula, R and R" represent H, R' represents —CH$_3$, the group VIII transition metal catalyst is a nickel catalyst and the halide promoter is HI.

10. A process as in claim 2 wherein, in the formula, R represents H, R' represents —CH$_3$, the group VIII transition metal catalyst is dicobalt octacarbonyl and the halide promoter is methyl iodide.

11. A process for preparing monocarboxylic acids which comprises bringing a glycol formate or an alkyl ether derivative thereof into contact with activated carbon having a density of about 0.03 to about 2.5 cm.$^3$ per gram and a surface area of about 200 to about 2,000 m$^2$ per gram in the presence of carbon monoxide and a catalyst system consisting essentially of about 10 to about 1,000 parts per million, based on said glycol formate, of a soluble group VIII transition metal catalyst and about 1 to 20 mol %, based on said glycol formate of a hydrogen iodide, a C$_1$ to C$_{12}$ alkyl halide or a benzyl bromide promoter, under reaction conditions including a temperature in the range of about 200° C. to about 400° C. and a pressure within the range of about 500 to about 4,000 psig to thereby provide a reaction product containing monocarboxylic acids but not a detectable quantity of polycarboxylic acids, said monocarboxylic acids being derived from the glycol of said glycol formate or said alkyl ether thereof and containing an additional carbon atom derived from reaction of the formate group of said glycol formate or said alkyl ether derivative thereof and said carbon monoxide, said glycol formate and said alkyl ether derivative thereof having the formula:

$$R'-O-\underset{R}{\overset{}{C}}H-\underset{R''}{\overset{}{C}}H-O-\overset{O}{\overset{\|}{C}}H \quad (I)$$

where R and R'' represent H or —CH$_3$;
R' represents H, or R''', or $$-\overset{O}{\overset{\|}{C}}H, \; -\underset{R}{\overset{}{C}}H-\underset{R''}{\overset{}{C}}H-O-\overset{O}{\overset{\|}{C}}H, \; \text{or} \; -\underset{R}{\overset{}{C}}H-\underset{R''}{\overset{}{C}}H-OH, \text{ or}$$

$$-\underset{R}{\overset{}{C}}H-\underset{R''}{\overset{}{C}}H-O-R''',$$

and
R''' represents a C$_1$ to C$_{12}$ alkyl group.

12. A process as in claim 11, wherein the glycol formate is brought into contact with the activated carbon at a temperature within the range of about 200° to about 360° C. and a pressure within the range of about 1500 to about 2100 psig.

13. A process as in claim 12 wherein, in formula (I), R' represents H or $$-\overset{}{\underset{O}{\overset{\|}{C}}}H,$$

the group VIII transition metal catalyst is a cobalt catalyst and the halide promoter is an iodide or a bromide.

14. A process as in claim 13, wherein the glycol formate is propylene glycol diformate, the halide promoter is CH$_2$I$_2$ and the catalyst is cobalt (III) 2,4-pentanedionate.

15. A process as in claim 13, wherein the glycol formate is propylene glycol diformate, the halide promoter is benzyl bromide and the catalyst is cobalt (III) 2,4-pentanedionate.

16. A process as in claim 12 wherein, in the formula, R and R'' represent H, R' represents:

$$-\underset{R}{\overset{}{C}}H-\underset{R''}{\overset{}{C}}H-O-\overset{O}{\overset{\|}{C}}H, \; \text{or} \; -\underset{R}{\overset{}{C}}H-\underset{R''}{\overset{}{C}}H-OH$$

the group VIII transition metal catalyst is a nickel catalyst, and the halide promoter is CH$_2$I$_2$.

17. A process as in claim 12 wherein, in the formula, R and R'' represent H, R' represents:

$$-\underset{R}{\overset{}{C}}H-\underset{R''}{\overset{}{C}}H-O-\overset{O}{\overset{\|}{C}}H, \; \text{or} \; -\underset{R}{\overset{}{C}}H-\underset{R''}{\overset{}{C}}H-OH$$

the group VIII transition metal catalyst is cobalt (III) 2,4-pentanedionate and the halide promoter is CH$_2$Br$_2$.

18. A process as in claim 12 wherein, in the formula, R and R'' represent H, R' represents:

$$-\underset{R}{\overset{}{C}}H-\underset{R''}{\overset{}{C}}H-O-\overset{O}{\overset{\|}{C}}H, \; \text{or} \; -\underset{R}{\overset{}{C}}H-\underset{R''}{\overset{}{C}}H-OH$$

the group VIII transition metal catalyst is cobalt (III) 2,4-pentanedionate and the halide promoter is benzyl bromide.

19. A process as in claim 12 wherein, in the formula, R represents H, R' represents —CH$_3$, the group VIII transition metal catalyst is a nickel catalyst and the halide promoter is HI.

20. A process as in claim 12 wherein, in the formula, R represents H, R' represents —CH$_3$, the group VIII transition metal catalyst is dicobalt octacarbonyl and the halide promoter is methyl iodide.

* * * * *